(12) United States Patent
Lataillade et al.

(10) Patent No.: US 9,752,121 B2
(45) Date of Patent: Sep. 5, 2017

(54) IN VITRO MODELLING OF HAEMATOPOIETIC STEM CELL MEDULLARY NESTS: A TOOL FOR STUDYING THE REGULATION OF HAEMATOPOIESIS, EVALUATING THE NESTING POTENTIAL OF A HAEMATOPOIETIC GRAFT AND TESTING THE PHARMACOTOXICOLOGY OF MEDICAMENTS

(75) Inventors: Jean-Jacques Lataillade, Elancourt (FR); Marie-Caroline Le Bousse-Kerdiles, Bourg-la-Reine (FR)

(73) Assignees: ETAT FRANCAIS (MINISTERE DE LA DEFENSE), SERVICE DE SANTE DES ARMEES, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 356 days.

(21) Appl. No.: 14/238,898

(22) PCT Filed: Aug. 14, 2012

(86) PCT No.: PCT/EP2012/065905
§ 371 (c)(1),
(2), (4) Date: Jul. 10, 2014

(87) PCT Pub. No.: WO2013/024096
PCT Pub. Date: Feb. 21, 2013

(65) Prior Publication Data
US 2014/0349312 A1 Nov. 27, 2014

(30) Foreign Application Priority Data

Aug. 16, 2011 (FR) .................................. 11 57358

(51) Int. Cl.
*C12N 5/077* (2010.01)
*C12N 5/0775* (2010.01)
*C12N 5/0789* (2010.01)
*C12N 5/071* (2010.01)
*G01N 33/50* (2006.01)

(52) U.S. Cl.
CPC ......... *C12N 5/0647* (2013.01); *C12N 5/0697* (2013.01); *G01N 33/5023* (2013.01); *G01N 33/5047* (2013.01); *C12N 2500/02* (2013.01); *C12N 2501/125* (2013.01); *C12N 2501/145* (2013.01); *C12N 2501/26* (2013.01); *C12N 2502/1142* (2013.01); *C12N 2502/1171* (2013.01); *C12N 2502/1305* (2013.01); *C12N 2502/1311* (2013.01); *C12N 2502/1352* (2013.01); *C12N 2502/1358* (2013.01); *C12N 2502/28* (2013.01); *C12N 2533/18* (2013.01); *C12N 2533/70* (2013.01); *C12N 2533/90* (2013.01); *G01N 2500/10* (2013.01)

(58) Field of Classification Search
None
See application file for complete search history.

(56) References Cited

U.S. PATENT DOCUMENTS 5,914,121 A * 6/1999 Robey .................. C12N 5/0654
424/422
2011/0207166 A1* 8/2011 Vaiselbuh ............ C12N 5/0647
435/32

FOREIGN PATENT DOCUMENTS

JP 2010-220581 A 10/2010
WO 99/64566 A2 12/1999

OTHER PUBLICATIONS

Singbrant et al., "Defining the hematopoietic stem cell niche: the chicken and the egg conundrum", Journal of Cellular Biochemistry, Jun. 2011, pp. 1486-1490, vol. 112, No. 6.
Kiel et al., "Uncertainty in the niches that maintain haematopoietic stem cells", Nature Reviews, pp. 290-301, Apr. 2008, vol. 8, No. 4.
Braccini et al., "Three-dimensional perfusion culture of human bone marrow cells and generation of osteoinductive grafts", Stem Cells, Sep. 2005, pp. 1066-1072, vol. 23, No. 8.
Nakamura et al., "Effect of calcium ion concentrations on osteogenic differentiation and hematopoietic stem cell niche-related protein expression ion osteoblasts", Tissue Engineering Part A, pp. 2467-2473, vol. 16, No. 8, 2010.
Conrad et al., "Expansion and differentiation of haemopoietic progenitor cells on endothelialized hydroxyapatite under static conditions", British Journal of Haematology, Apr. 1999, pp. 40-49, vol. 105, No. 1.
De Barros et al., "Osteoblasts and Bone Marrow Mesenchymal Stromal Cells Control Hematopoietic Stem Cell Migration and Proliferation in 3D In Vitro Model", Plos One, Feb. 8, 2010, p. E9093, vol. 5, No. 2.
Calvi et al., "Osteoblastic cells regulate the haematopoietic stem cell niche", Nature, Oct. 23, 2003, pp. 841-846, vol. 425, No. 6960.
De Smedt et al., "Human bone marrow CD34<+> progenitor cells mature to T cells on OP9-DL1 stromal cell line without thymus microenvironment", Blood Cells, Molecules & Diseases, Nov. 1, 2004, pp. 227-232, vol. 33, No. 3.
Lymperi, S. et al. 2011 "Inhibition of osteoclast function reduces hematopoietic stem cell numbers in vivo" *Blood* 117(5): 1540-1549.

* cited by examiner

*Primary Examiner* — Allison Fox
(74) *Attorney, Agent, or Firm* — Knobbe Martens Olson & Bear, LLP (57) ABSTRACT

The present invention relates to a culture support for cultivating hematopoietic stem cells (HSCs) and/or hematopoietic progenitors (HPs), comprising a calcium biomaterial, osteoclasts, endothelial cells and mesenchymatous stem cells (MSCs) and/or osteoblasts and/or adipocytes. The present invention also relates to a method for preparing such a culture support, and an in vitro HSC and/or HP cultivation method. The use of such a culture support for studying cellular mechanisms involved in hematopoiesis and/or differentiation of HSC/HPs and/or for studying the efficacy and/or the toxicity of a medicament candidate is also described.

15 Claims, 4 Drawing Sheets

FIG.4

IN VITRO MODELLING OF HAEMATOPOIETIC STEM CELL MEDULLARY NESTS: A TOOL FOR STUDYING THE REGULATION OF HAEMATOPOIESIS, EVALUATING THE NESTING POTENTIAL OF A HAEMATOPOIETIC GRAFT AND TESTING THE PHARMACOTOXICOLOGY OF MEDICAMENTS The present invention relates to a support for cultivating hematopoietic stem cells (HSCs) and/or hematopoietic progenitors (HPs), comprising a calcium biomaterial, osteoclasts, endothelial cells and mesenchymatous stem cells (MSCs) and/or osteoblasts and/or adipocytes. The present invention also relates to a method for preparing such a culture support and to an in vitro method for culturing HSCs and/or HPs. The use of such a culture support for studying cell mechanisms involved in hematopoiesis and/or differentiation of HSCs/PHs, and/or for studying the efficiency and/or the toxicity of a drug candidate is also described.

BACKGROUND OF THE INVENTION

Adult hematopoiesis

Hematopoiesis is the physiological process which allows the production and continuous and regulated renewal of the whole of the formed elements of blood from a small contingent of cells called hematopoietic stem cells (HSCs). In human adults, hematopoiesis lies in bone marrow within specific localizations (called niches) where it is closely regulated by the means of secreted factors and/or direct interactions with the cell component and the extracellular matrix which surround it, which form the <<microenvironment>>. Deregulation of this process in many cases leads to the development of malignant hemopathies. Study of the regulation of hematopoiesis at different levels of its differentiation (HSCs, immature progenitors, committed progenitors, mature and functional cells) has given the possibility of emphasizing the importance of the microenvironment and of the signals which it generates. Indeed, it is the development of co-cultivation systems of hematopoietic cells on stromal medullary cells which, by mimicking a microenvironment, has given in vitro access to the study of myelopoiesis and lymphopoiesis B as well as of immature progenitors LTC-IC (Long Term Culture-Initiating Cells). In vitro lymphopoiesis T, as for it, has only been possible in the presence of a thymic microenvironment or directly in organ-typical cultures of the FTOC (Fetal Thymic Organ Culture) type. Its study on medullary stroma was recently made possible by modifying these stromas (overexpression of Delta like-1 by gene transfer) (De Smedt et al, Blood Cells Mol Dis, 2004, 33(3):227-32).

These data emphasize the importance of better understanding the signals emitted by the microenvironment for studying and analyzing normal or pathological hematopoiesis in its global component. This is all the more important since several recent studies conducted on mice suggest that perturbations of the hematopoietic microenvironment/of niches may lead to development of myeloproliferative syndromes (MPS). Also in humans, an increasing number of arguments are in favor of the role of the microenvironment in the pathogenesis of leukemias and MPSes by providing an environment favorable to the development of the pathological clone, to the detriment of normal hematopoiesis. This assumption is supported by the observation of development of MPSes in certain allografted patients, while the relevant donors do not develop any of them.

Medullary Niches with Hematopoietic Stem Cells

Although the concept of a hematopoietic niche was introduced for the first time in 1978 by Schofield, it is only from the beginning of the years 2000 that a set of experimental arguments contributes to demonstration of its existence.

Present knowledge of the hematopoietic microenvironment reports the existence of two niches regulating the HSCes and respectively called endosteal niche and vascular niche. The endosteal niche is located in contact with the bone and is made of osteoblasts, fibroblasts and adipocytes which all originate from the mesenchymatous stem cell (MSC), as well as of osteoclasts deriving from HSCs and involved in bone resorption. Very recent studies show that osteoblasts and adipocytes may derive from Nestin$^+$ MSC, the quiescence, proliferation and differentiation of which would be regulated by the sympathetic nervous system (SNS), therefore suggesting the role of the central nervous system in the modeling of the niches, the regulation of the HSCs and their mobilization. The vascular niche, as for it, consists in a network of fenestrated vessels, consisting of endothelial cells, deriving from endothelial stem cells (ESCs). So-called <<CAR>> (CXCL12 Abundant Reticular) cells present in bone marrow, would also participate in the forming of these niches via the production of CXCL12/SDF-1.

HSCs maintain constant dialog with their niche, where they are regulated via direct contacts with different stromal cells as well as through microenvironmental factors (concentrations of $Ca^{2+}$ and of $O_2$). A certain number of ligands/receptors pairs such as angiopoietin-1/Tie2, Jagged/Notch, Frizzled/Wnt, Sonic Hedgehog/Patched, as well as adherence molecules of the VLA4, VLA5, CD44, N-cadherin type are involved in the interactions between the osteoblast and HSC, and would regulate the quiescence/self-renewal equilibrium of the latter. Further, the SP (Side Population) functionality for drug exclusion, one of the characteristics of the HSCs, may be intimately related to their localization within the niches and notably endosteal niches. The diffusible factors as for them are represented by certain hormones (parathyroid hormone, serotonin, . . . ) BMPs (bone morphogenic proteins), cytokines (SCF, VEGF, TPO . . . ) and chemokines (CXCL12/SDF-1, IL8 . . . ).

The endosteal niche, center of a relative hypoxia to the contact of the bone, would be involved in maintaining stem cells in a quiescent state, via interactions with osteocompetent cells of the mesenchymatous line (osteoblasts, adipocytes, fibroblasts) and of the hematopoietic line (osteoclasts and endothelial cells).

In addition to its structural role of support, the extracellular matrix (ECM) also operates as a key regulator in the proliferation/differentiation/survival of HSCs/HPs within the niches. Among the components of this matrix, structural proteins are found including collagens and elastin, specialized proteins such as fibronectin and laminin, and regulatory proteins like metalloproteases and proteoglycans. Proteoglycans form a family of proteins, the major benefit of which is borne by its chains of glycosaminoglycans (GAGs). These GAGs intervene in the bioavailability of growth factors and of chemokines and protect them from their proteolytic degradation.

At the present time, while the impact of the bone system on hematopoiesis begins to be better known, little work has studied the mutual role of hematopoiesis in the physiology of bone remodeling. The vascular niche, where the oxygen concentration is higher, would rather be involved in the proliferation and differentiation of HSCs, although recent work has shown the importance of endothelial cells in the self-renewal of HSCs. However, to this day, it has definitively not been established whether both of these niches are distinct, or if they contribute to a common niche.

Understanding the Regulation of Hematopoiesis and Testing the Pharmacotoxicology of Medicaments The mechanisms involved in the interactions between HSCs and osteocompetent cells within their regulatory niches still remain poorly known, whether in physiology or pathology. The understanding of these mechanisms is in fact limited because of the absence of an in vitro tool enabling studying hematopoiesis in a global context in particular integrating its microenvironmental aspects.

On the other hand, the development of novel therapeutic molecules requires the development of tests suitable for evaluating their toxicity and their efficacy on hematopoiesis and potentially on bone remodeling. Such a tool therefore has a major benefit on cognitive, pharmacological and therapeutic levels, in particular in hematology (di Maggio et al, Biomaterials, 2011, 32(2):321-9). Indeed, presently, there does not exist any culture system or only very few, allowing the study of normal or pathological hematopoiesis in the context of its microenvironment: the <<niche>> component is either absent (liquid culture in cytokine conditions), or restricted and poorly adapted (co-cultivation on stromal lines) or non-accessible (in vivo experimentation, graft). Among the rare studies reported to this day, the developed models are limited to interactions between certain stromal cells and HSCs, and they do not take into account the niche in its globality (de Barros et al, PLoS One, 2010, 8; 5(2)).

Therefore there is a major benefit in modeling a two-dimensional (2D) or three-dimensional (3D) niche in order to have an in vitro tool accessible and adjustable for studying hem atopoiesis in a context closer to physiology.

The object of the present invention is therefore to propose a 2D or 3D model of a hematopoietic niche, recreating the complexity of the medullary environment.

The invention consists of performing cellularization of biological (decellularized bone fragments) or manufactured supports, of variable calcium richness, with different types of stromal cells (osteoblasts, osteoclasts, adipocytes, mesenchymatous cells, endothelial cells) and of co-cultivating, on these cellularized supports, stem cells or hematopoietic progenitors (SP, ALDH$^{strong}$, CD34$^+$, Lin$^-$ ... ). Constituents of the extracellular matrix (GAG, fibronectin, collagens ... ) are grafted on these supports in order to ensure good bioavailability of the factors produced by the stromal cells. In order to reproduce as close as possible the concentration variations of oxygen of the medullary microenvironment, the co-cultures are made at concentrations of $O_2$ varying from 0.1% to 20%, preferentially from 1% to 3%.

This model enables revealing the SP potential of stem cells and could form an in vitro evaluation test of the nesting potential of a hematopoietic graft. It also allows study of the role of the cellular and humoral elements forming the hematopoietic niche on the cycling, proliferation, differentiation and mobilization of HSCs. This system will also allow study of the role of hematopoietic cells on osteocompetent cells and bone remodeling. Finally this model can be used as a pharmacological and toxicological tool for testing in vitro new drugs targeting hematological diseases and which may affect the cellular elements forming the hematopoietic niche. This model may therefore be used for pharmacological and toxicological studies of medicaments. This tool also allows the study of the role of hematopoietic niches in the deregulation of hematopoiesis characterizing certain malignant hemopathies.

DESCRIPTION OF THE INVENTION

Culture Support

A first aspect of the invention corresponds to a culture support of hematopoietic stem cells (HSCs) and/or hematopoietic progenitors (HPs), comprising:
 a. a calcium biomaterial;
 b. osteoclasts;
 c. endothelial cells; and
 d. mesenchymatous stem cells (MSCs) and/or osteoblasts and/or adipocytes.

The culture support of hematopoietic stem cells (HSCs) and/or hematopoietic progenitors (HPs) according to the invention comprises a cell component and an acellular component, called a <<calcium biomaterial>>, which plays the role of an osteoconductive support. The calcium biomaterial may be simple or multiple, so that the cells forming the culture support and the cultured cells may be seeded on a same biomaterial or on different biomaterials (of identical or different natures), for example one per cell type. By <<different biomaterials>> are meant individualized entities stemming from a same biomaterial or from biomaterials having different compositions.

The composition of the calcium biomaterial may vary. The calcium biomaterial may comprise or consist of hydroxyapatite (HA) and of tricalcium phosphate (TCP). For example, the calcium biomaterial may correspond to decellularized bone fragments or synthetic materials. The proportions of HA and TCP may vary. By varying the proportions of both of these constituents, it is for example possible to obtain biomaterials having different porosities. In particular, the HA proportion of the biomaterial may vary between 55% and 75%, preferably between 60% and 70%. The TCP proportion of the biomaterial may vary between 25% and 45%, preferably between 30% and 40%.

The calcium biomaterial is two-dimensional or three-dimensional. The use of a calcium biomaterial of the three-dimensional type may in particular give the possibility of carrying out the culture of HSCs and/or HPs under these physiological conditions closer to those present within the natural hematopoietic niche.

According to a specific embodiment, the calcium biomaterial is selected from the group consisting of biomaterials of the B2D type or B3D type (BD Biocoat Osteologic Bone Cell Culture System) and of Calciresorb 35 (Ceraver, France). The biomaterials of B2D and B3D are multiphase synthetic materials based on calcium phosphate which have excellent biocompatibility and are suitable for allowing proliferation and differentiation of cells of many types. The B3D biomaterial displays a cross-linked structure with open pores and has ideal pore size and porosity for studies in vitro. Calciresorb 35 is a mixture of synthetic β tricalcium phosphate $Ca_3(PO_4)_2$ and hydroxyapatite $Ca_{10}(PO_4)_6(OH)_2$, in the form of porous blocks. This biphasic ceramic is composed of 65% HA and of 35% of βTCP. Its porosity is of about 45%, the total porosity consisting of macroporosity (pores from 100 to 400 μm) and of microporosity (pores of less than 10 μm).

The cells constituting the cell component of the culture support according to the invention may have different origins. In particular they may stem from human bone marrow. Bone marrow mononuclear cells may for example be isolated from cancellous bone fragments from operating residues of patients operated for a total hip prosthesis. The endothelial cells comprised in the culture support according to the invention may also stem from cells isolated from the blood of the patient, such as blood circulating endothelial progenitors (CEP) present in the peripheral blood or blood mononuclear hematopoietic cells.

Osteoclasts may be obtained from hematopoietic progenitors by specific differentiation. The osteoclast phenotype may for example be validated by May Grumwald Giemsa (MGG) staining with which it is possible to show the multinuclear aspect resulting from the fusion of osteoclast cells, and by showing tartrate acid resistant phosphatase activity (TRAP).

The endothelial cells comprised in the culture support according to the invention are non-engaged hematopoietic cells (said to be of <<negative lineage>> or Lin−). Further, they express the CD144 and KDR molecules at their surface. Endothelial cells of the invention may for example be obtained from mononuclear cells of bone marrow, by carrying out immunomagnetic depletion of <<positive lineage>> cells (allowing the removal of the majority population of engaged hematopoietic cells), and then CD144/KDR sorting. The sorted-out cells may then be cultivated in an endothelial medium. The endothelial culture medium may for example be the medium of the EMG2-MV type marketed by Lonza or an equivalent medium. The endothelial progenitors may also be obtained from peripheral blood (PEC). For this, the colonies derived from PECs are generated by adherence to plastic from mononuclear cells obtained from 20 mL of blood.

The culture support according to the invention moreover comprises MSCs and/or osteoblasts and/or adipocvtes. In particular, the culture support according to the invention may comprise MSCs or osteoblasts or adipocytes.

The MSCs may stem from human bone marrow and be isolated by adherence to plastic. For example, MSCs may be obtained by cultivating mononuclear cells of bone marrow isolated from fragments of cancellous bone from operating residues of patients operated for a total hip prosthesis. In the case when the culture support comprises MSCs, the latter are then differentiated into osteoblasts and/or adipocytes, as described hereafter for the method for preparing the culture support. They are characterized, as regards their phenotype, by co-expression of a certain number of markers such as for example CD73, CD90, CD105, CD146, and by the absence of expression of other markers, in particular CD45 and CD34.

The culture support according to the invention may comprise osteoblasts, which may for example stem from specific differentiation of MSCs. The osteoblast phenotype may be evaluated in a phase contrast microscope by appreciating the mineralization level, by immunohistochemistry by showing the alkaline phosphatase (ALP) activity by means of a chemical reaction with naphthol AS-Biphosphate, and by indirect immunofluorescence (IFI) with detection of osteocalcin, osteopontin and ALP.

The culture support according to the invention may comprise adipocytes, which may for example stem from specific differentiation of MSCs. The adipocytes nature of the cells may be checked by examination with a phase contrast microscope showing the presence of lipid vacuoles and by immunohistochemical staining with oil red O binding to the lipid vacuoles.

According to a particular embodiment, the culture support according to the invention further comprises one or more component(s) of the extracellular matrix (ECM).

The expression <<components of the extracellular matrix>> designates any compound entering the composition of the extracellular matrix. Compounds forming the extracellular matrix are well known to one skilled in the art and for example include natural glycosaminoglycans (GAG), fibronectin, collagens, hyaluronic acid, laminin and elastin. The components of the extracellular matrix according to the invention may also correspond to mimetics of GAG. Indeed, the latter have the advantage of not being degraded by glycanases. According to a specific embodiment of the invention the components of the extracellular matrix are natural GAGs, GAG mimetics, fibronectin, collagens and/or hyaluronic acid. Preferably the GAG mimetics used are those marketed by OTR3 (Organ, Tissue, Regeneration, Repair and Replacement) under the name of RGTAs for <<ReGeneraTing Agents>>. When they are associated to the culture support according to the invention, the components of the extracellular matrix are preferentially used at a concentration from 80 to 100 ng/mL.

According to a particular embodiment, the culture support according to the invention further comprises a biological glue.

The expression <<biological glue>> designates any compound of biological origin enabling maintaining the cells together and in contact with biomaterials. The compounds which may be used as a biological glue are known to one skilled in the art. The biological glue may for example be obtained from plasma (biological glue of the fibrin glue type), or from plasma rich in platelets (biological glue of the platelet gel type).

Method for Preparing a Culture Support

Another aspect of the invention relates to a method for preparing a culture support according to the invention, comprising steps consisting of grafting a calcium biomaterial with osteoclasts, endothelial cells and mesenchymatous stem cells (CSM) and/or osteoblasts and/or adipocytes, and optionally one or more component(s) of the ECM.

The preparation of a culture support according to the invention requires sharing the different stromas in a same well. In a first phase, the osteoclasts, the endothelial cells and the MSCs and/or osteoblasts and/or adipocytes forming the niche may be seeded on one or several 2D or 3D biomaterials. If MSCs are use, the latter may subsequently be differentiated into osteoblasts and/or adipocytes. Hybrid BMs cellularized by the different types of stromal cells are thus obtained. The latter may be gathered in a single well containing the whole of the hybrid BMs in order to form the culture support according to the invention. Alternatively, cultures of each differentiated cell type may be carried out in the form of balls, i.e. by preventing them from adhering to the support during their differentiation. The different cell types may then be mixed and seeded on a same and single biomaterial, as described by de Barros et al. (PLoS One, 2010, 8; 5(2)).

HSCs/HPs may subsequently be added onto the culture support. The concentration of these HSCs/HPs may vary. Preferentially, the HSC/HP concentration is comprised between $5.10^4$ and $2.10^5$ cells per ml and per well, even more preferentially, the HSC/HP concentration is comprised between $10^5$ and $2.10^5$ cells per ml and per well.

The osteoclasts may be obtained from hematopoietic progenitors by specific differentiation. In general, the differentiation of hematopoietic progenitors begins by a Lin⁻ depletion carried out on an affinity column in order to remove the differentiated cells expressing the following lines antigens: CD2, CD3, CD11b, CD14, CD15, CD16, CD19, CD56, CD123, GPA. The thereby obtained Lin⁻ cells may then be cultivated on biomaterials in the presence of a cocktail of cytokines for example comprising SCF, Flt3L and TPO at a concentration varying from 10 to 50 ng/ml. After 5 days of cultivation, the culture medium may be replaced with a myeloid differentiation medium containing the following cytokines: SCF, Flt3L, TPO, IL-6 and GM-CSF at a concentration varying from 10 to 50 ng/ml. After 15 days of cultivation, the cells may be incubated in an osteoclastic induction medium containing M-CSF, RANK-L and IL-6 at a concentration varying from 10 to 20 ng/ml. The quality of the differentiation may be controlled on a well not containing any biomaterial. The osteoclastic phenotype may for example be checked by May Grumwald Giemsa (MGG) staining giving the possibility of showing the multinuclear aspect, resulting from the fusion of osteoclastic cells, and by showing the tartrate acid resistant phosphatase (TRAP) activity.

When MSCs are grafted on the culture support, these cells are then differentiated into osteoblasts or adipocytes. For this, the MSCs may be distributed into two batches, and then each of the batches is cultivated in the presence of a set of growth factors and/or of specific cytokines, in order to induce differentiation of the MSCs of one batch into osteoblasts, and the differentiation of the MSCs of the other batch into adipocytes.

The induction of differentiation of the osteoblasts from MSCs may be achieved by adding into the culture medium dexamethasone, L-ascorbic acid 2-phosphate and β-glycerophosphate. The differentiation may be observed after 3 weeks of cultivation in this induction medium. These induction molecules may be used at concentrations comprised between 0.05 μM and 0.2 μM for dexamethasone, between 0.04 mM and 0.06 mM for L-ascorbic acid 2-phosphate and between 8 mM and 12 mM for β-glycerophosphate. The preferred concentrations for these induction molecules are the following: 0.1 μM for dexamethasone, 0.05 mM for L-ascorbic 2-phosphate acid and 10 mM for β-glycerophosphate.

The quality of the differentiation of the osteoblasts may then be evaluated by various techniques well known to one skilled in the art. For example, the quality of the differentiation may be evaluated in a phase contrast microscope by appreciating the mineralization level, by immunohistochemistry by detecting alkaline phosphatase activity (ALP) by a chemical reaction with naphthol AS-Biphosphate, and by indirect immunofluorescence (IFI) with detection of osteocalcin, osteopontin and ALP. In particular, the IFI reactions may be conducted after binding with 4% paraformaldehyde followed by saturation/permeabilization with PBS enriched with 3% bovine albumin and 0.1% of Triton X100. The anti-osteocalcin, anti-osteopontin and anti-PAL antibodies may be incubated in a PBS solution enriched with 1% bovine albumin and 0.05% Tween 20 and then the labellings are revealed by an antibody targeting murine immunoglobulins coupled with phycoerythrin. Finally, counter-staining with Hoechst allowing the nuclei to be viewed may be performed.

The differentiation of the adipocytes may be induced from MSC by treatment with dexamethasone, 3-isobutyl-1-methylxanthin (IBMX), indomethacin and insulin for nine days. These molecules may be used at concentrations comprised between 0.05 μM and 0.2 μM for dexamethasone, between 0.4 mM and 0.6 mM for 3-isobutyl-1-methylxanthin (IBMX), between 0.1 mM and 0.3 mM for indomethacin and between 0.005 mg/ml and 0.02 mg/ml for insulin. The preferred concentrations for these molecules are the following: 1 μM for dexamethasone, 0.5 mM for 3-isobutyl-1-methylxanthin (IBMX), 0.2 mM for indomethacin and 0.01 mg/ml for insulin.

The adipocyte nature of the cells may then be confirmed by examination in a phase contrast microscope showing the presence of lipid vacuoles and by immunohistochemical staining with oil red O binding the lipid vacuoles.

According to a specific embodiment, the differentiated osteoblasts and adipocytes are grafted on two distinct culture supports or on a same culture support.

The cultivation of the different cell types forming the support of the invention may be conducted either in normoxia, i.e. at a relative oxygen concentration of 20%, either in a hypoxic condition closer to the physiological situation in bone marrow, i.e. at oxygen concentrations comprised between 1 and 5%, preferably 3%. According to a specific embodiment, the preparation of the culture support is carried out under conditions such that the oxygen content is comprised between 1 and 5%. For example, the preparation of the culture support may be carried out in a chamber or in an incubator, in which the oxygen content may be measured by means of a probe and automatically adjusted to a determined value.

In Vitro Method for Culturing HSC and/or HP

Another aspect of the invention relates to an in vitro method for culturing hematopoietic stem cells (HSCs) and/or hematopoietic progenitors (HPs), comprising the steps consisting of:
a. seeding at least one culture support as defined above with hematopoietic stem cells (HSCs) and/or hematopoietic progenitors (HPs); and
b. cultivating said hematopoietic stem cells (HSCs), and/or hematopoietic progenitors.

The HSCs/HPs may be obtained from medullary or blood mononuclear hematopoietic cells. The cells not expressing any differentiation antigens such as for example CD2, CD3, CD11b, CD14, CD15, CD16, CD19, CD56, CD123, GPA (so-called <<negative lineage>> or <<Lin−>> cells) may be isolated by sorting after staining with a cocktail of antibodies targeted against various differentiation antigens such as for example the <<Lineage cell depletion kit>>, marketed by Miltenyi Biotec. The sorting may in particular be carried out by depletion on an automaton.

The inventors have shown that in vitro cultivation of HSCs/HPs on a culture support as defined in the invention promotes expansion of the CD34+ cells from a population of peripheral blood Lin− cells.

Further, the inventors have shown that the in vitro cultivation of HSC/HP on a culture support as defined in the invention promotes the maintaining or the acquisition of the SP functionality. The expression <<SP functionality>> designates the capability of stem cells, in particular HSCs, of causing effluence of the fluorescent coloring agent Hoechst-33342 or other coloring agents or drugs. This functionality may for example be evaluated by flow cytometry, by quantification of the residual fluorescence of the cells in the form of a characteristic cytogram, the cells having the strongest effluence capability being considered as the most primitive (Goodell et al, Methods Mol Biol, 2005, 290:343-52).

Also, in a specific embodiment, the HSCs/HPs cultivated on the culture support according to the invention do not express differentiation antigens (Lin−), express a high level of fluorescence corresponding to a high level of ALDH enzymatic activity (($ALDH^{strong}$), express at their surface CD34 (CD34+) and have the SP function. Identification or selection of Lin−, $ALDH^{strong}$ or CD34+ cells may be carried out as detailed in Example 1.

Briefly, the SP function may be determined by incubating Lin− cells in the presence of Hoechst-33342, for example at 1-10 μg/ml in DMEM+2% fetal calf serum, in an amount of 0.25.10$^6$ to 2.10$^6$ cells/mL. The incubation is preferentially carried out at 37° C. for 60 to 120 min, in particular for 90 min. The cells are then centrifuged at 4° C. and the cell pellet is resuspended in HBSS without Ca$^{2+}$, or Mg$^{2+}$, under cold conditions at a concentration of 2 to 4.10$^6$ cells/mL. The effluences of Hoechst-33342 may then be measured by flow cytometry.

The determination of the ALDH activity may be carried out by using ALDEFLUOR technology which uses the substrate Bodipy™-AminoAcetAldehyde Diethyl Acetal (BAAA-DA) of the ALDH-A1 enzyme. This substrate is dissolved in DMSO and exposed to the action of HCl in order to being converted into BAAA, a fluorescent substrate of the enzyme. The cells are incubated in the presence of BAAA, for example at a concentration of 1.5 µM at 37° C., which is converted by ALDH into a fluorescent product (BAA) retained in the cells. In the incubation buffer ALDE-FLUOR, the cells which express a high level of ALDH are those which have a high fluorescence level, as measured in the FL1 channel (FITC fluorescence) in flow cytometry.

The CD34$^+$ cells may be purified from mononuclear cells stemming from a sample of allogenic marrow by separation according to a Ficoll gradient and by then taking up the pellet in a PBS buffer enriched with 2% human albumin (Vialebex, LFB) and 0.5% of human polyvalent immunoglobulins (Tegeline, LFB) and incubation for at least 5 minutes. The CD34$^+$ cells may then be purified by any suitable method, for example by incubation in the presence of an anti-CD34 antibody coupled with magnetic beads and by separation on an immunomagnetic column.

The in vitro cultivation of HSCs/HPs on the culture support is preferably carried out in a suitable culture medium. Media adapted to the cultivation of cells in vitro are well known to one skilled in the art. These may be in particular defined synthetic media either added with serum or not. The suitable culture medium for in vitro cultivation of HSCs/HPd may for example correspond to SynH (Abcell-Bio) or to STEM ALPHA.A (Stem Alpha). Generally, the cultivation is carried out until the cultivated cells reach the desired differentiation level. The differentiation level of the cells may be evaluated according to the phenotype of the cells. The cells may for example be cultivated until they exhibit a primitive phenotype such that they do not express differentiation antigens (Lin−), that they express a high ALDH enzyme level (ALDH$^{strong}$), that they express at their surface CD34 (CD34+) and that they have the SP function.

In a particular embodiment, the in vitro cultivation of HSC/HP on the culture support is carried out in the presence of a candidate compound. In particular, the candidate compound may be a medicament candidate, for example enabling preventing or treating pathologies related to deregulation of hematopoiesis, such as certain malignant hemopathies. The presence of the candidate compound in the culture medium may give a possibility of conducting pharmacology or toxicology studies on this compound. The efficiency of the compound may for example be tested by comparing the phenotypes of the cells present in the culture, following cultivation in the presence or in the absence of the candidate compound. The toxicity of the compound may for example be tested by evaluating the amount or the proportion of apoptotic or necrotic cells present in the culture, following cultivation in the presence or in the absence of the candidate compound.

Use of the Culture Support

The mechanisms involved in the interactions between HSCs and osteocompetent cells within their regulatory niches still remain poorly known both in physiology and pathology. The understanding of these mechanisms is actually limited because of the absence of in vitro tools allowing study of hematopoiesis in a global context, in particular integrating its microenvironmental aspects.

The culture support of the invention may allow study of the role of cellular and humoral elements forming the hematopoietic niche, on the cycling, proliferation, differentiation and mobilization of the HSCs. The culture support may also allow study of the role of hematopoietic cells on osteocompetent cells and bone remodeling.

Also, another aspect of the invention deals with the use of the culture support according to the invention for studying cell mechanisms involved in hematopoiesis and/or differentiation of the HSCs/HPs.

The culture support of the invention enables revealing the SP potential of stem cells. Thus, it may allow in vitro evaluation of the nesting potential of a hematopoietic graft.

Also, another aspect of the invention deals with the use of the culture support according to the invention for evaluating the nesting potential of a hematopoietic graft.

Up to now, no suitable cultivation system existed for studying normal or pathological hematopoiesis in the context of its microenvironment. The culture support according to the invention can be used as an in vitro tool accessible and adjustable for studying hematopoiesis in a context closer to physiology. Such a tool has a major benefit on the pharmacological and therapeutic levels in particular on hematology. Indeed, the development of novel therapeutic molecules requires the development of suitable tests for evaluating their toxicity and their efficiency on hematopoiesis and potentially on bone remodeling. The culture support according to the invention can advantageously be used as a tool for pharmacological and toxicological studies of drugs, notably for in vitro testing of new drugs targeting hematological diseases and which may affect the cell elements forming the hematopoietic niche. Finally, the culture support according to the invention may also allow the study of the role of hematopoietic niches in the deregulation of hematopoiesis characterizing certain malignant hemopathies.

Also, another aspect of the invention deals with the use of the culture support according to the invention for studying the efficiency and/or the toxicity of a medicament candidate.

Kit

A last aspect of the invention relates to a kit comprising:
a. a calcium biomaterial;
b. osteoclasts, or a set of cytokines and/or growth factors allowing differentiation of HSCs in osteoclasts;
c. endothelial cells, or a set of cytokines and/or growth factors allowing differentiation of circulating endothelial progenitors or mononuclear cells of the bone marrow into endothelial cells;
d. mesenchymatous stem cells (MSCs) and/or osteoblasts and/or adipocytes and optionally a set of cytokines and/or growth factors allowing differentiation of the MSCs into osteoblasts and/or adipocytes; and/or differentiation of the osteoblasts and/or of the adipocytes; and
e. optionally one or more component(s) of the extracellular matrix (ECM)

The cytokines and/or growth factors allowing differentiation of HSCs into osteoclasts and comprised in the kit according to the invention may for example include the following cytokines/growth factors: SCF, Flt3, TPO, IL-6 and GM-CSF, M-CSF, and/or RANK-L. The preferred concentrations for these growth factors are the following: 10 ng/ml for SCF, Flt3, TPO, IL-6 and GM-CSF, and 20 ng/ml for M-CSF, RANK-L and IL-6.

Cytokines and/or growth factors allowing differentiation of circulating endothelial progenitors or mononuclear cells of bone marrow into endothelial cells and comprised in the kit according to the invention may, for example include VEGF, bFGF, EGF and IGF-1.

The molecules allowing differentiation of the MSCs into osteoblasts and/or differentiation of the osteoblasts comprised in the kit according to the invention may for example include dexamethasone, L-ascorbic acid 2-phosphate and β-glycerophosphate. These molecules may be used at concentrations comprised between 0.05 μM and 0.2 μM for dexamethasone, between 0.04 mM and 0.06 mM for L-ascorbic acid 2-phosphate and between 8 mM and 12 mM for β-glycerophosphate. The preferred concentrations for these growth factors are the following: 0.1 μM for dexamethasone, 0.05 mM for L-ascorbic acid 2-phosphate and 10 mM for β-glycerophosphate.

The molecules allowing differentiation of the MSCs into adipocytes and/or differentiation of the adipocytes comprised in the kit according to the invention may for example include dexamethasone, 3-isobutyl-1-methylxanthine (IBMX), indomethacin and insulin. These molecules may be used at concentrations comprised between 0.05 μM and 0.2 μM for dexamethasone, between 0.4 mM and 0.6 mM for 3-isobutyl-1-methylxanthin (IBMX), between 0.1 mM and 0.3 mM for indomethacin and between 0.005 mg/ml and 0.02 mg/ml for insulin. The preferred concentrations for these growth factors are the following: 1 μM for dexamethasone, 0.5 mM for 3-isobutyl-1-methylxanthin (IBMX), 0.2 mM for indomethacin and 0.01 mg/ml for insulin.

The invention will be described in more detail in the following figures and examples.

SHORT DESCRIPTION OF THE FIGURES

FIG. 1. Procedure for Preparing a 2D or 3D Culture Support According to the Invention The preparation of a culture support according to the invention requires the sharing of different stromas in a same well. In a first phase, the osteoclasts, the endothelial cells and the MSCs forming the niche may be seeded on one or several 2D or 3D biomaterials. The MSCs may subsequently be differentiated into osteoblasts and/or adipocytes. Hybrid BMs cellularized by the different types of stromal cells are thus obtained. The letters may then be gathered in a single well containing the whole of the hybrid BMs, in order to form the culture support according to the invention.

A population of Lin$^-$ cells from peripheral blood of non-mobilized healthy subjects, having an initial richness in CD34$^+$ cells equivalent to 30%, was cultivated for 7 days on a 2D culture support according to the invention. At the end of this culture, the population of CD34$^+$ represents about 96.25%+/−1.71% (n=4) of the produced viable cells.

In order to validate the capability of the culture support according to the invention of maintaining a pool of primitive hematopoietic cells, the maintaining of the SP functionality of the Lin$^-$ medullary cells was evaluated after 3 to 7 days of culture. For this purpose, Lin$^-$ medullary cells (2.10$^5$) were cultured in the presence or in the absence of 2D cellularized culture support (n=3 à 4). In the presence of a cellularized culture support with MSCs and/or MSCs differentiated into osteoblasts, the percentage of SP cells (1.46+/−0.33) is maintained relatively to the first day (before cultivation: 1.02+/−0.03, NS), or even increased as compared with the condition without any cellularized culture support (0.05+/−0.01, p<0.01) and with the transwell condition (0.17+/−0.05, p<0.05).

Lin$^-$ medullary cells were cultured in the presence or in the absence of 2D cellularized culture support with MSCs.

EXAMPLES

Example 1

Preparation of Various Cell Types Forming the Niche

Isolation and Culture of Mesenchymatous Stem Cells (MSCs)

Mononuclear cells of bone marrow are isolated from fragments of cancellous bones from operating residues of patients operated for a total hip prosthesis and seeded into 75 cm$^2$ flasks at a concentration of 100,000 cellules/cm$^2$ in a medium based on MEMα (ATGC/biological Industries) containing 10% fetal calf serum (SVF, Hyclone) and 1% ciprofloxacin (Bayer). The culture flasks are incubated at 37° C. in an atmosphere containing 5% of $CO_2$ and 20% of $O_2$. The culture medium is renewed after three days of culture, the first week and then once a week until quasi-confluence (80% to 90%). When the cells have reached confluence, they are detached from the plastic support by enzymatic action of trypsin (trypsin 1: 250, Sigma) during 5 min at 37° C., numbered (trypan blue) and then frozen in a cryoprotective solution containing 5% human albumin and 10% DMSO. With view to their use, the MSCs are then thawed in a water bath at 37° C. and then diluted again and washed in a medium consisting of MEMα, 1% ciprofloxacin and 20% albumin. After numbering and evaluating the viability by staining with trypan blue, the MSCs are then seeded under different experimental conditions described below in a culture medium based on MEMα, 10% SVF, 1% ciprofloxacin. The culture medium is renewed once a week until the cells attain 80% confluence. They are then trypsinated and reseeded for a second passage.

Osteoblast and Adipocyte Differentiation of MSCs

Osteoblast differentiation: Osteoblast differentiations are induced from MSCs brought to confluence in a medium of MEMα, 10% SVF, 1% ciprofloxacin enriched with 0.1 μM of dexamethasone, 0.05 mM of L-ascorbic acid 2 phosphate and 10 mM of β-glycerophosphate (Sigma). The induction media are renewed twice a week for three weeks. The quality of the differentiation is evaluated with a phase contrast microscope by appreciating the mineralization level, by immunohistochemistry by detecting the alkaline phosphatase activity (PAL) by a chemical reaction with naphthol AS-Bi-phosphate (Sigma), and by indirect immunofluorescence (IFI) with detection of osteocalcin, osteopontin and ALP. The IFI reactions are conducted after binding with 4% paraformaldehyde (Sigma) followed by saturation/permeabilization by PBS enriched with 3% bovine albumin and 0.1% of Triton X100 (Prolabo). The anti-osteocalcin, anti-osteopontin and anti-ALP antibodies are incubated in a PBS solution enriched with 1% bovine albumin and 0.05% Tween 20 (Bio-rad), and then the labelling are revealed by an antibody targeting the murine Igs coupled with phycoerythrin (goat antimouse-PE; Caltag). Finally, counter-staining with Hoechst allowing the viewing of the nuclei is performed (Hoechst 33258, Molecular Probes).

Adipocyte differentiation: The adipocyte differentiations are induced from sub-confluent MSCs with three treatment cycles with 1 μM of dexamethasone, 0.5 mM of 3-isobutyl-1-methylxanthin (IBMX), 0.2 mM of indomethacin and 0.01 mg/ml of insulin (Sigma). Each treatment cycle lasts for three days, the last cycle ending with three days of maintenance in a specific medium (10% FCS supplemented with 0.01 mg/ml of insulin). The adipocyte nature of the culture is confirmed by examination in a phase contrast microscope showing the presence of lipid vacuoles and by immunohistochemical staining with oil red O binding the lipid vacuoles.

Osteoclast Differentiation from Hematopoietic Progenitors

The mononuclear cells of human bone marrow obtained from fragments of cancellous bone from operating residues of patients operated for a total hip prosthesis are separated by a density gradient on a Ficoll cushion and then cultured for one night, in an incubator at 37° C., in a humid atmosphere containing 5% $CO_2$. The next day, a $Lin^-$ depletion is carried out on an affinity column in order to remove the differentiated cells expressing the following lines antigens: CD2, CD3, CD11b, CD14, CD15, CD16, CD19, CD56, CD123, GPA. The thereby obtained $Lin^-$ cells (about $10^7$ cells) are cultured on HA/TCP biomaterials in a medium containing a cocktail of cytokines (SCF, Flt3 and TPO at 10 ng/ml). The $Lin^-$ cells ($2.10^6$ $Lin^-$ cells) are plated on 2D or 3D biomaterials. After 5 days of cultivation, the culture medium is replaced with a myeloid differentiation medium containing the following cytokines: SCF, Flt3, TPO, IL-6 and GM-CSF at 10 ng/ml. After 15 days of cultivation, the cells are incubated in an osteoclast induction medium containing M-CSF, RANK-L and IL-6 at 20 ng/ml.

The quality of the differentiation is controlled on a well not containing any biomaterial. The osteoclastic phenotype is determined by May Grumwald Giemsa (MGG) staining giving the possibility of showing the multi-nuclear aspect, resulting from the fusion of osteoclast cells, and by detection of the tartrate acid resistant phosphatase activity (TRAP).

Obtaining Endothelial Cells

The endothelial cells may be obtained from two sources:
1) blood-circulating endothelial progenitors (ECPs) from peripheral blood. For this, the colonies derived from the ECPs are generated from mononuclear cells obtained from 20 mL of blood. Each colony produces about $10^6$ cells after 2 passages. Thus, after 3 or 4 passages, it is possible to obtain up to $10^8$ functional endothelial cells.
2) mononuclear cells of the bone marrow. The first step consists in immunomagnetic depletion of the positive lineage cells allowing removal of the majority population of engaged hematopoietic cells. On the Lin− population, CD144/KDR sorting is then performed, and the sorted cells are cultivated in an endothelial medium. The isolated medullary endothelial cells then rapidly proliferate in this medium.

Isolation of Hematopoietic Stem Cells (HSCs)/Hematopoietic Progenitors (HPs)

$Lin^-$: The medullary or blood mononuclear hematopoietic cells are obtained after centrifugation on a Ficoll Hypaque density gradient. Then the $Lin^-$ cells (negative lineage) are sorted after labelling with a cocktail of antibodies targeted against various differentiation antigens (Lineage cell depletion kit, Miltenyi Biotec). After washing in a buffer medium, sorting is performed by depletion on an automaton (Automacs, Miltenyi Biotech).

SP: The Lin– cells are incubated in the presence of Hoechst-33342 (5 μg/ml), an intercalator of DNA, in an amount of $10^6$ cells/ml in DMEM containing 2% FCS. The cells are then incubated for 90 mins at 37° C.; the remainder of the experiment is conducted under cold conditions in order to avoid passive effluence of Ho by cells not expressing the pumps. The cells are then centrifuged for 15 mins at 4° C. and at 1,500 rpm and the cell pellet is re-suspended in HBSS without $Ca^{2+}$, or $Mg^{2+}$, under cold conditions at a concentration from 2 to $4.10^6$ cells/ml.

$ALDH^{strong}$: ALDEFLUOR technology uses the Bodipy™-AminoAcetAldehyde Diethyl Acetal (BAAA-DA substrate) of the ALDH-A1 enzyme. This substrate is dissolved in DMSO and exposed to the action of HCl so as to be converted into BAAA, a fluorescent substrate of the enzyme. The cells are incubated in the presence of BAAAA (1.5 μM) at 37° C. which diffuses through the plasma membranes of the viable cells. The ALDH enzyme converts this substrate into a fluorescent product (BAA) which is then retained inside the cells due to its negative charge and to the polarity of the cell membranes. The ALDEFLUOR incubation buffer contains an inhibitor of MDR effluence pumps. Therefore, the cells which express a high level of ALDH are those which retain the BAA within their cytoplasm, but also those which have a high fluorescence level. This fluorescence may be measured in the FL1 channel (FITC fluorescence) in flow cytometry.

$CD34^+$: The $CD34^+$ cells are purified from mononuclear cells stemming from an allogenic marrow sample. The mononuclear cells are separated according to a Ficoll gradient and the pellet is diluted in a PBS buffer enriched with 2% human albumin (Vialebex, LFB) and 0.5% of human polyvalent immunoglobulins (Tegeline, LFB) and then incubated for 5 minutes so as to saturate the receptors non-specific to immunoglobulins (Ig) present at the surface of the $CD34^+$ cells. The cells are then incubated in the presence of an anti-CD34 antibody coupled with magnetic beads (20 $\mu l/10^8$ cells; Clinimacs, Miltenyi Biotech) for 30 minutes and then washed in PBS-2% albumin (PA) before being loaded on an immunomagnetic column (Automacs, Miltenyi Biotech). The cells may then be frozen in 5% albumin, 10% dimethylsulfoxide (DMSO, Sigma). The quality of the sorting is controlled by flow cytometry so as to evaluate the $CD34^+$ cell purity in the final cell suspension.

Example 2

Selection of the Biomaterials

Modeling the niche requires the sharing of different stromas on a same osteoconductive 2D or 3D support. These biomaterials (BMs) may comprise in particular hydroxyapatite (HA) and of tricalcium phosphate (TCP) in various proportions and have variable porosities. From among the latter, let us mention B2D and B3D (BD Biocoat Osteologic Bone Cell Culture System) and Calciresorb 35 (Ceraver) which is a biphasic ceramic comprising 65% of HA and 35% of βTCP. The results shown in Example 5 were obtained with Calciresorb 35 (Ceraver).

Example 3

Selection of the Extracellular Matrix

Natural glycosaminoglycans (GAG) or their mimetics (which have the advantage of not being degraded by glycanases) may be associated with the biomaterial. The preferentially used mimetic GAGs are marketed by OTR3 (for Organ, Tissue, Regeneration, Repair and Replacement) under the name of RGTAs for <<ReGeneraTing Agents>> and are ideally used at a concentration from 10 to 50 mg/ml. The results shown in Example 5 were obtained with OTR4131.

Example 4

Modeling of the Hematopoietic Niche in 2D or 3D

Figure 1:
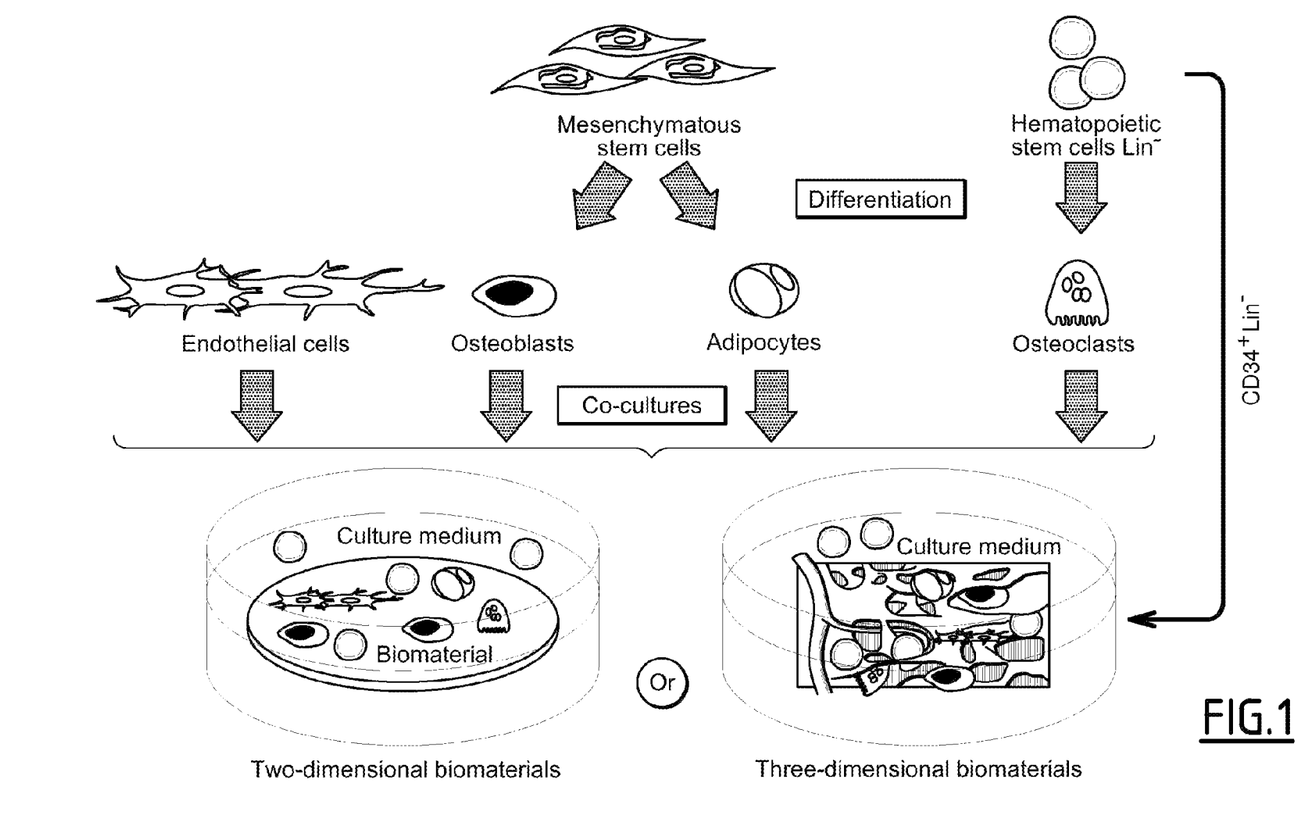

The modeling of the niche requiring the sharing of the various stromas in a same well, the MSCs, the osteoclasts and the endothelial cells are ideally seeded on a same BM or on different 2D or 3D BMs (one per cell type) (FIG. 1). The results shown in Example 5 were obtained by seeding on various 3D BMs of the Calciresorb 35 type. The MSCs are induced towards osteoblast and adipocyte differentiations. Hybrid BMs cellularized by the different types of stromal cells are thereby obtained. The latter are then collected in a single well containing the whole of the hybrid BMs in which HSCs/HPs are then added at variable concentrations in order to produce co-cultures. The results shown in Example 5 were obtained after adding Lin⁻ cells to the concentration of $1.10^5$ cells/ml/wells. An alternative to this procedure consists of producing cultures of each differentiated cell type in the form of balls (by preventing them from adhering to the support during their differentiation). The different cell types are then mixed and seeded on a single and same biomaterial (De Barros et al., PLoS One. 2010; 5(2), page 11, 3rd paragraph).

In detail, in the case of the preparation of various types of stromal cells on independent BMs, the BMs are individually seeded in microtubes at a concentration of $5.10^4$ to $2.10^5$ cells per ml and per BM. After 3 hours of incubation at 37° C. in atmosphere enriched with 5% $CO_2$, the cellularized BMs are transferred into a microplate (four well) in a MEMα medium, 10% FCS, 1% ciprofloxacin in order to achieve the osteoblast and adipocyte inductions, 2 to 5 days later. The osteoblast induction period is limited to fourteen days since the BMs induce per se self-induction of the MSCs towards the osteoblast line. Several BM <<controls>> (one per cell type) are analyzed in immunohistochemistry by reaction with naphthol AS-Biposphate and by staining with oil red O so as to confirm the positive nature of the osteoblast and adipocyte differentiations.

The HSCs/PHs are thawed on the day of their being put into a co-culture and diluted in the SYNH medium (95L01HSA, AbCys) containing 1% ciprofloxacin, enriched with hematopoietic growth factors (FCH, 10 ng/mL): thrombopoietin (Tpo, Peprotech), stem cell factor (SCF, Peprotech) and Flt3-ligand (RetD System). The quality of the thawed samples is evaluated by flow cytometry (expression of CD34) and by culture in a semi-solid medium. The thawed cells are then seeded ($5.10^4$ to $2.10^5$ cells per well) in the presence of different hybrid BMs to form a niche and then cultured for 1 to 2 weeks in the previously defined SYNH medium.

These cultures are achieved either in a relative oxygen concentration of 20%, or in a hypoxic condition closer to the physiological situation in bone marrow, i.e. at concentrations between 1 and 5%. The results shown in Example 5 were obtained under conditions of a relative oxygen concentration of 3%.

Example 5

Biological Characterization of the Niche

Characterization of the Different Cell Types of the Niche

The evaluation of the osteoblast, adipocyte and osteoclast differentiation with tests of specific induction is carried out by staining, as described in Example 1.

Functional Evaluation of the Niche

Evaluation of the Factors Secreted by the 3D Niche

The main molecules involved in the regulation of hematopoiesis and produced inside the thereby modeled niches were quantified by an ELISA test after 7 days of co-culture in the presence of HSC/HP CD34⁺. The results are expressed in pg/ml per $10^5$ stromal cells (MSCs, osteoblasts, osteoclasts and adipocytes) and $5.10^4$ initially seeded CD34⁺ cells. Table 1 below shows a significant production of various factors; the osteoblasts and the MSCs being the majority of producing cells. These results testify the functional capability of the cells forming the thereby modeled niches.

TABLE 1

Evaluation of the factors secreted by a cellularized niche

| Factor | Concentration at D7 (pg/ml) |
|---|---|
| Osteopontin | 17000 ± 5000 |
| Osteoprotegerin | 9 ± 7 |
| Flt3-L | 21000 ± 8000 |
| Interleukine 8 | 4500 ± 3500 |
| Interleukine 6 | 5000 ± 100 |
| Stem Cell Factor | 5900 ± 100 |
| Angiopoietin 1 | 800 ± 40 |
| Hepatocyte Growth factor | 1700 ± 50 |
| SDF1 | 380 ± 80 |

Evaluation of the Stromal Cell Power of the Modeled 2D and 3D Niches

Figure 2:
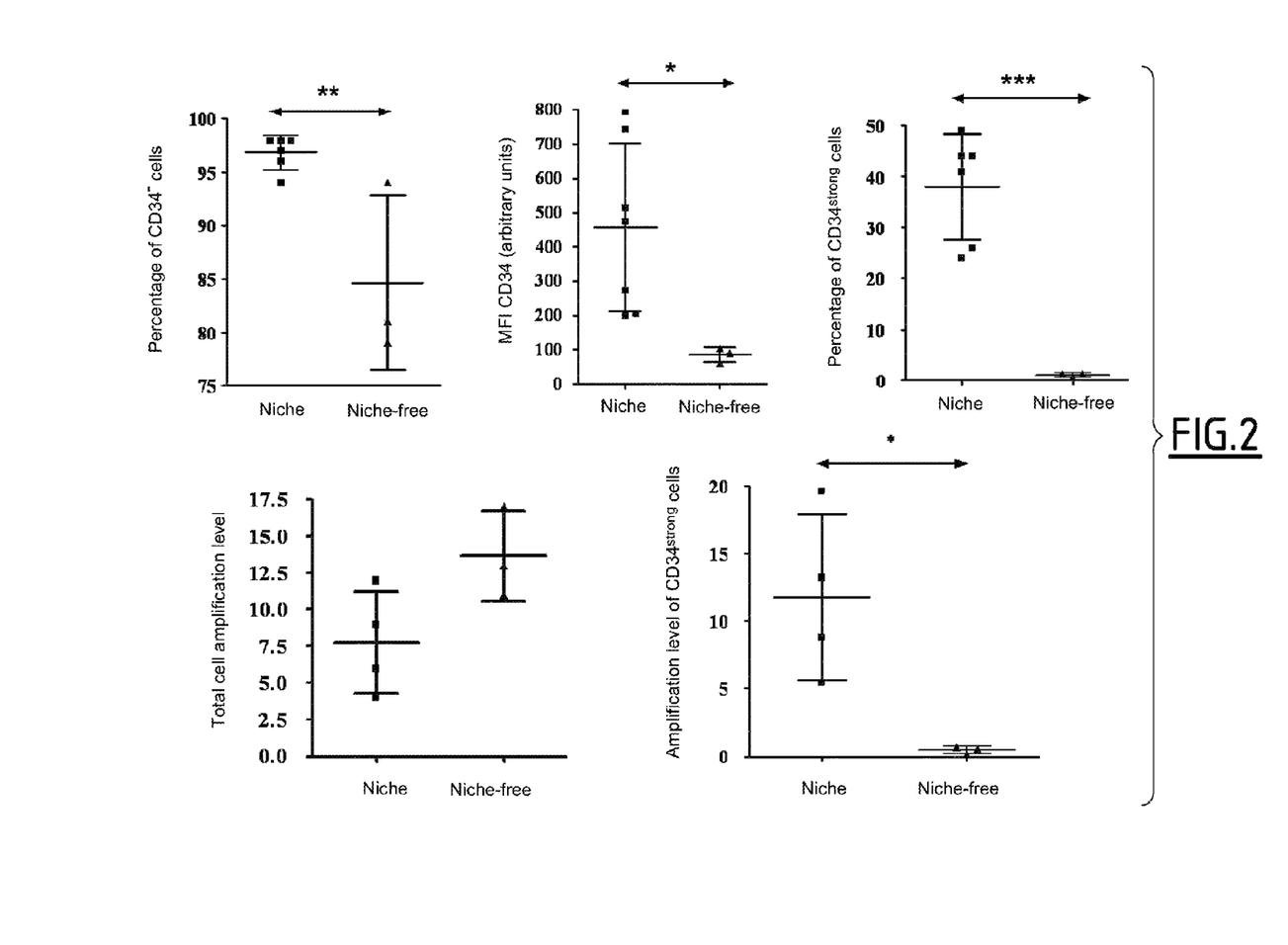
FIG. 2. Expansion of the CD34$^+$ Cells on a 2D Culture Support According to the Invention (*=p<0.05; **=p<0.01)

The 2D modeled niches (osteoblasts, adipocytes, MSCs and osteoclasts) promote expansion of the CD34⁺ cells from a population of Lin⁻ cells from peripheral blood of non-mobilized healthy subjects (richness in CD34⁺ cells equivalent to 30%). The results show that after 7 days of co-culture, the CD34⁺ population represents about 96.25%+/−1.71% (n=4) of the produced viable cells (FIG. 2).

The percentage of CD34⁺ cells is significantly higher than that observed in the so-called <<niche-free>> condition, i.e. in the presence of biomaterials not colonized by stromal cells (97%+/−2% vs 85%+/−8%; p<0.05). Although the proliferation rate of the total cells is slightly smaller under the niche conditions (7.75%+/−3.5%) relatively to niche-free conditions (13.67%+/−3.06%; not significant), the amplification rate of the number of CD34$^{Strong}$ cells within the niches is about 3.5 times higher than on day 0. On the contrary, when the CD34 cells are cultivated under <<niche-free>> conditions, the number of CD34$^{Strong}$ cells is less than the initial figure. The thereby modeled niches allow amplification of the CD34$^{Strong}$ cells to the detriment of the CD34$^{Weak}$ cells, which suggests that taking into account the niche may be of interest in the optimization of the culture procedures of CD34$^{Strong}$ cells, giving the possibility of promoting proliferation to the expense of differentiation.

Moreover, when the CD34⁺ cells are separated from the 2D niche by a transwell system, the results in terms of the maintaining of the number of CD34⁺ cells are inferior to the condition reproducing a complete niche, which suggests the importance of cell contacts and of the factors secreted in majority by the stromal cells in this process.

Evaluation of the Maintaining/Acquisition of the SP Functionality by Modeled Niches In order to validate the capability of the hematopoietic niches of maintaining a pool of primitive hematopoietic cells, we also evaluated their capability of maintaining the SP functionality of the Lin⁻ medullary cells after 3 to 7 days of culture. The SP functionality is defined by the capability of the stem cells and in particular of the HSCs of causing effluence of the fluorescent coloring agent Hoechst-33342 or of other coloring agents and drugs. This functionality may be evaluated by flow cytometry by quantification of the residual fluorescence of the cells in the form of a characteristic cytogram, the cells having the greatest effluence capability being considered as the most primitive. For this purpose, we cultivated Lin⁻ medullary cells ($2.10^5$) in the presence or in the absence of 2D cellularized niches (n=3 to 4).

Figure 3:
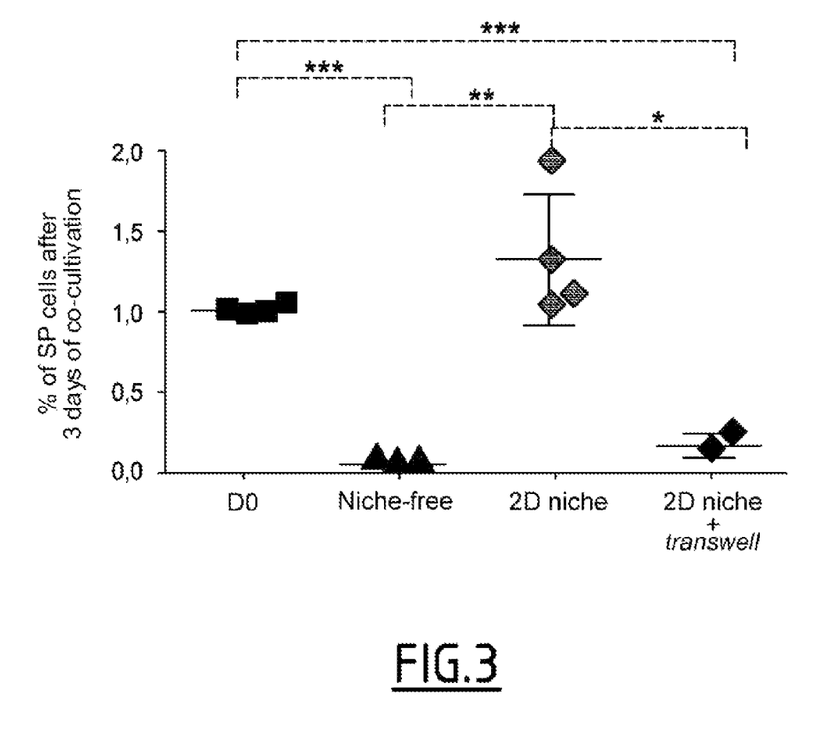
FIG. 3. Evaluation of the Maintaining/Acquisition of the SP Functionality of Cells Cultivated on a Culture Support According to the Invention.

FIG. 3 shows that in the presence of cellularized niches (osteoblasts, adipocytes, osteoclasts, MSCs), the Lin⁻ medullary cells preserve their SP functionality, as compared with co-cultures on non-cellularized biomaterials (niche-free condition) or in a transwell system (Boyden condition). Thus, in the presence of a cellularized niche, the percentage of SP cells (1.46+/−0.33) is maintained relatively to the first day (before cultivation: 1.02+/−0.03, NS), or even increased as compared with the niche-free condition (0.05+/−0.01, $p<0.01$) and to the transwell condition (0.17+/−0.05, $p<0.05$). Thus, in terms of the absolute number of SP cells, the culture on a 2D niche gives the possibility of maintaining the pool of SP cells in a co-culture for three days (about 2920, in the presence of a niche), which is not the case in the absence of a niche or in a transwell condition (about 100, in the absence of a niche). These results suggest that the cellular interaction between the stromal cells and hematopoietic cells are required for maintaining the SP functionality.

Figure 4:
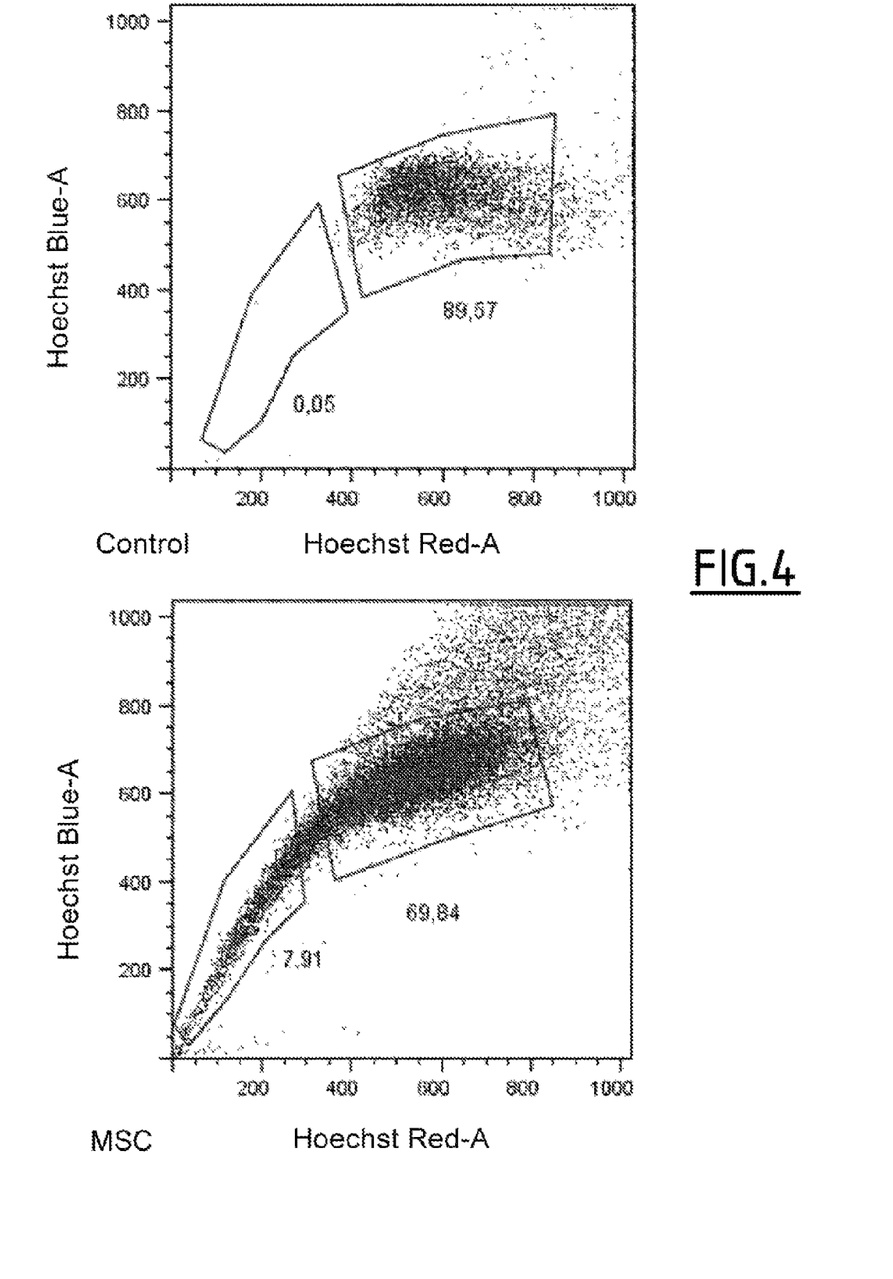
FIG. 4. Effect of the MSCs on the Acquisition of an SP Functionality

Unlike the HSCs/HPs of bone marrow, the cells of the peripheral blood do not express the SP functionality. When the latter were seeded for 3-5 days on a model niche, a certain percentage (0.5 to 2%) of them acquired SP functionality. Experiments conducted by using the various cell constituents separately show that the MSCs seem to have a predominate role in this acquisition (FIG. 4).

The invention claimed is:

1. A culture support for hematopoietic stem cells (HSCs) and/or hematopoietic progenitors (HPs), consisting of:
   a. a calcium biomaterial, which is a decellularized bone fragment or a synthetic calcium biomaterial;
   b. osteoclasts;
   c. endothelial cells;
   d. mesenchymatous stem cells (MSCs) and/or osteoblasts and/or adipocytes; and
   e. optionally one or more component(s) of extracellular matrix (ECM),
   wherein the osteoclasts, the endothelial cells and the mesenchymatous stem cells (MSCs) and/or osteoblasts and/or adipocytes are grafted on the calcium biomaterial, and wherein the culture support is capable of in vitro or ex vivo supporting proliferation of HSCs and/or HPs.

2. The culture support according to claim 1, wherein said calcium biomaterial comprises hydroxyapatite (HA) and tricalcium phosphate (TCP).

3. The culture support according to claim 1, wherein the calcium biomaterial comprises 55% to 75% hydroxyapatite and 25% to 45% tricalcium phosphate.

4. The culture support according to claim 1, wherein the calcium biomaterial comprises 60% to 70% hydroxyapatite and 30% to 40% tricalcium phosphate.

5. A culture support for hematopoietic stem cells (HSCs) and/or hematopoietic progenitors (HPs), consisting of:
   a. a calcium biomaterial, which is a decellularized bone fragment or a synthetic calcium biomaterial;
   b. osteoclasts;
   c. endothelial cells;
   d. one or more components of extracellular matrix (ECM) grafted on the calcium biomaterial;
   e. mesenchymatous stem cells (MSCs) and/or osteoblasts and/or adipocytes; and
   f. optionally, one or more component(s) of extracellular matrix (ECM),
   wherein the osteoclasts, the endothelial cells and the mesenchymatous stem cells (MSCs) and/or osteoblasts and/or adipocytes are grafted on the calcium biomaterial, and wherein the culture support is capable of in vitro or ex vivo supporting proliferation of HSCs and/or HPs.

6. The culture support according to claim 1, wherein the endothelial cells are Lin- CD144+ KDR+ cells.

7. A culture support for hematopoietic stem cells (HSCs) and/or hematopoietic progenitors (HPs), consisting of:
   a. a calcium biomaterial, which is a decellularized bone fragment or a synthetic calcium biomaterial;
   b. osteoclasts;
   c. endothelial cells;
   d. mesenchymatous stem cells (MSCs) and/or osteoblasts and/or adipocytes;
   e. hematopoietic stem cells (HSCs) and/or hematopoietic progenitors (HPs); and
   f. optionally one or more component(s) of extracellular matrix (ECM),
   wherein the osteoclasts, the endothelial cells, the MSCs and/or osteoblasts and/or adipocytes, and the HSCs and/or HPs are grafted on the calcium biomaterial, and wherein the culture support is capable of in vitro or ex vivo supporting proliferation of the HSCs and/or the HPs.

8. A culture support for hematopoietic stem cells (HSCs) and/or hematopoietic progenitors (HPs), consisting of:
   a. calcium biomaterial, which is a decellularized bone fragment or a synthetic calcium biomaterial;
   b. osteoclasts;
   c. endothelial cells;
   d. one or more component(s) of extracellular matrix (ECM) grafted on the calcium biomaterial; and
   e. mesenchymatous stem cells (MSCs) and/or osteoblasts and/or adipocytes; and
   f. optionally, one or more component(s) of the ECM,
   wherein the osteoclasts, the endothelial cells and the mesenchymatous stem cells (MSCs) and/or osteoblasts and/or adipocytes are grafted on the calcium biomaterial, and wherein the culture support is capable of in vitro or ex vivo supporting proliferation of HSCs and/or HPs.

9. A culture support for hematopoietic stem cells (HSCs) and/or hematopoietic progenitors (HPs), consisting of:
   a. a calcium biomaterial, which is a decellularized bone fragment or a synthetic calcium biomaterial;
   b. osteoclasts;
   c. endothelial cells;
   d. a biological glue;
   e. mesenchymatous stem cells (MSCs) and/or osteoblasts and/or adipocytes; and
   f. optionally, one or more component(s) of extracellular matrix (ECM), wherein the osteoclasts, the endothelial cells and the mesenchymatous stem cells (MSCs) and/or osteoblasts and/or adipocytes are grafted on the calcium biomaterial, and wherein the culture support is capable of in vitro or ex vivo supporting proliferation of HSCs and/or HPs.

10. A method for preparing a culture support as defined in claim 1, comprising the steps of grafting the calcium biomaterial with osteoclasts, endothelial cells and mesenchymatous stem cells (MSCs) and/or osteoblasts and/or adipocytes and optionally one or more component(s) of the ECM.

11. An in vitro method for culturing hematopoietic stem cells (HSCs) and/or hematopoietic progenitors (HPs), comprising the steps of:
   a. seeding at least one culture support as defined in claim 1 with hematopoietic stem cells (HSCs) and/or hematopoietic progenitors (HPs); and
   b. culturing said hematopoietic stem cells (HSCs) and/or hematopoietic progenitors (HPs).

12. A method for studying the cellular mechanism involved in hematopoiesis and/or differentiation of hematopoietic stem cells (HSCs) and/or hematopoietic progenitors (HPs), said method comprising the steps of:
   a. culturing hematopoietic stem cells (HSCs) and/or hematopoietic progenitors (HPs) on a culture support as defined in claim 1, and
   b. determining the ALDH enzymatic activity and/or the SP functionality and/or the expression level of the differentiation antigens (Lin-) and/or the expression level of surface CD34.

13. A method for evaluating the nesting potential of a hematopoietic graft, said method comprising the steps of:
   (a) culturing hematopoietic stem cells (HSCs) and/or hematopoietic progenitors (HPs) on a culture support as defined in claim 1; and
   (b) evaluating the capability of the cells cultured at step (a) of causing effluence of a fluorescent coloring agent, wherein level of effluence of a fluorescent coloring agent corresponds to nesting potential.

14. The method of claim 13, wherein the coloring agent is Hoechst-33342.

15. A method for studying the efficiency and/or the toxicity of a medicament candidate, said method comprising the steps of:
   (a) culturing hematopoietic stem cells (HSCs) and/or hematopoietic progenitors (HPs) on a culture support as defined in claim 1 in the presence or in the absence of the medicament candidate,
   (b) comparing the phenotypes of the cells present in the cultures obtained at step (a) in the presence or in the absence of the medicament candidate, and/or evaluating the amount or the proportion of apoptotic or necrotic cells present in the cultures obtained at step (a) in the presence or in the absence of the medicament candidate, and
   (c) deducing the efficiency and/or the toxicity of the medicament candidate from the results obtained at step (b).

* * * * *